United States Patent [19]

Pilgram

[11] 4,149,872

[45] Apr. 17, 1979

[54] N-PYRIDINYL UREA AND CYCLOPROPANECARBOXAMIDE HERBICIDES

[75] Inventor: Kurt H. G. Pilgram, Modesto, Calif.

[73] Assignee: Shell Oil Company, Houston, Tex.

[21] Appl. No.: 817,895

[22] Filed: Jul. 21, 1977

[51] Int. Cl.$^2$ .................. A01N 9/22; C07D 213/75
[52] U.S. Cl. .................................. 71/94; 546/292;
546/306; 546/308; 546/309
[58] Field of Search .... 260/295 AM, 295 E, 294.8 R, 260/294.8 F, 295.5 A, 295.5 D; 71/94, 118

[56] References Cited

U.S. PATENT DOCUMENTS

| | | | |
|---|---|---|---|
| 3,246,975 | 4/1966 | Hopkins et al. | 71/2.5 |
| 3,277,107 | 10/1966 | Neighbors | 260/306.8 |
| 3,277,171 | 10/1966 | Hopkins | 260/557 |
| 3,306,727 | 2/1967 | Neighbors | 71/2.6 |
| 3,328,156 | 6/1967 | Hopkins | 71/118 |
| 3,376,309 | 4/1968 | Foster et al. | 260/295 |
| 3,467,753 | 9/1969 | Foster et al. | 424/263 |
| 3,682,934 | 8/1972 | Martin et al. | 260/295.5 D |
| 4,030,910 | 6/1977 | Johnston | 71/94 |
| 4,046,553 | 9/1977 | Takahashi et al. | 71/94 |

Primary Examiner—Richard Raymond

[57] ABSTRACT

Compounds of the formula

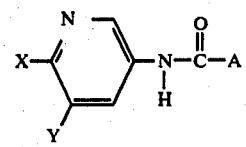

wherein A is

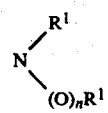

in which $R^1$ is alkyl and n is 0–1, or

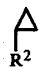

in which $R^2$ is hydrogen, alkyl or halogen; Y is halogen or alkyl; and X is halogen, —$NR^3R^4$ in which $R^3$ and $R^4$ each independently is hydrogen or alkyl; $OR^5$; $SR^5$; $S(O)R^5$ or $S(O)_2R^5$, in which $R^5$ is alkyl, are useful as herbicides.

13 Claims, No Drawings

N-PYRIDINYL UREA AND CYCLOPROPANECARBOXAMIDE HERBICIDES

BACKGROUND OF THE INVENTION

1. Field of the Invention

This invention relates to certain N-pyridinyl ureas and cyclopropanecarboxamides, their use as herbicides and to herbicidal compositions containing these amides and ureas.

2. Description of the Prior Art

U.S. Pat. No. 3,376,309 and a division thereof, U.S. Pat. No. 3,467,753, broadly disclose a variety of pyridinyl amides and ureas for use as fungicides, particularly for systemic applications where any adverse effects to the plant itself would appear undesirable. U.S. Pat. Nos. 3,426,975, 3,277,107, 3,227,171, 3,306,727 and 3,328,156 generically disclose various cycloalkanecarboximide herbicides and specifically N-(2-pyridinyl) cyclopropanecarboxmide.

SUMMARY OF THE INVENTION

The present invention is directed to new compounds having the formula I

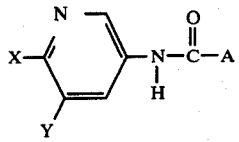

wherein
A is

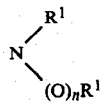

in which $R^1$ is an alkyl group containing from 1 to 6 carbon atoms and n is an integer of 0–1, or

in which $R^2$ is a hydrogen atom, an alkyl group containing from 1 to 4 carbon atoms, or a halogen atom having an atomic number from 9 to 35, inclusive;

Y is a halogen atom having an atomic number of from 9 to 35, inclusive, or an alkyl group containing from 1 to 6 carbon atoms; and X is a halogen atom having an atomic number of from 9 to 35, inclusive, —$NR^3R^4$ in which $R^3$ is a hydrogen atom or an alkyl group containing from 1 to 6 carbon atoms and $R^4$ is independently a group as for $R^3$ or a cycloalkyl group containing from 3 to 7 ring carbon atoms and 3 to 11 carbon atoms; $OR^5$; $S(O)R^5$; $S(O)_2R^5$; or $SR^5$ in which $R^5$ is an alkyl group containing from 1 to 6 carbon atoms.

Examples of species contemplated within the scope of the invention include:

N-((5-bromo-6-(isopropylsulfonyl)-3-pyridinyl)-1-chlorocyclopropanecarboxamide

N-((5-bromo-6-(isobutylsulfinyl)-3-pyridinyl)cyclopropanecarboxamide

N-(5-methyl-6-((1-methylcyclopropyl)amino)-3-pyridinyl)-1-butylcyclopropanecarboxamide N-(5-chloro-6-(isopropylsulfonyl)-3-pyridinyl)1-ethyl-cyclopropanecarboxamide N-((5-ethyl)-6-(isopropoxy)-3-pyridinyl)-N'N'-dimethylurea N-(5-fluoro-6-ethylsulfinyl-3-pyridinyl)-N'N'-dimethylurea N-(5-methyl-6-chloro-3-pyridinyl)-N',N'-dimethylurea One subclasss of compounds of the invention are those of formula I wherein A is

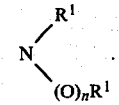

Preferred because of their herbicidal properties are those wherein each $R^1$ is methyl. Also preferred are compounds wherein n is 1.

Another subclass of compounds of the invention are derivatives of cyclopropanecarboxylic acids. Examples wherein $R^2$ in the formula is alkyl include methyl, ethyl, propyl, n-butyl and the like or wherein $R^2$ is halogen including fluorine, chlorine or bromine. Because of their herbicidal properties compounds wherein $R^2$ is methyl or hydrogen are preferred, particularly methyl.

The group Y can be chlorine, bromine, fluorine, methyl, ethyl or the like. Preferred because of their herbicidal properties and ease of preparation are compounds of formula I wherein Y is chlorine.

The group X can be $OR^5$, $SR^5$, $S(O)R^5$, $S(O)_2R^5$ in which $R^5$ is an alkyl group containing from 1 to 4 carbon atoms, preferably branched chain; such as isopropyl or tertiary butyl. Preferably X is halogen; —$NR^3R^4$ in which $R^3$ is a hydrogen atom, an alkyl group containing from 1 to 4 carbon atoms and $R^4$ is independently a group as for $R^3$ or is 1-methylcyclopropyl; or $OR^5$ in which $R^5$ is an alkyl group containing 2 or 3 carbon atoms.

The compounds of the invention can be prepared by introduction of desired substituents into the 2- and 3-positions of a 5-nitropyridine. 2-Substituted-3-halo-5-nitropyridine can be prepared by halogenation of 2-hydroxy-5-pyridines for example with chlorine or bromine. Displacement of bromine by fluorine can be used to prepare 3-fluoro derivatives. The hydroxy group can then be converted to the desired 2-substituent by alkylation to produce compounds where X in formula I is $OR^5$ or by displacing the hydroxy group with chlorine and subsequent displacement of the chlorine by the appropriate amine or mercaptan. Sulfides resulting from the latter can then be oxidized to yield sulfonyl or sulfinyl substituents, if desired. 2-Substituted-3-alkyl-5-nitropyridines can be prepared by forming a salt, e.g. lithium salt, of 3-picoline. An alkyl group is then introduced at the 3-position. Treatment with sodium hydride followed by nitric acid and then by sodium nitrite-hydrochloric acid provides 5-nitro-2-hydroxy-3-alkyl-1-pyridines which can then be treated as described above. Reduction of the nitro group and acylation of the resulting amine with the desired cyclopropanecarbonyl chloride, N-alkoxy-N-alkylcarbamoyl chloride or dialkylcarbamoyl chloride in the presence of triethylamine at more or less ambient temperatures yields the desired products. Ureas of the invention can also be prepared by reacting a pyridyl isocyanate with an acylamine or by reacting an aminopyridine with a dialkylamine or alkoxyalkylamine.

The compounds of the invention have been found to be useful for controlling undesirable plant growth. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broadleafed weeds. Some of the compounds are particularly useful as selective herbicides for control of weeds in certain important crops.

The invention includes plant growth regulating compositions comprising a carrier or a surface-active agent, or both a carrier and a surface-active agent, and, as active ingredient, at least one compound of formula I. Likewise the invention also includes a method of controlling plant growth which comprises applying to the locus an effective amount of a compound of formula I.

The term "carrier" as used herein means a solid or fluid material, which may be inorganic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and sytrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous comounds. Mixtures of different liquids are often suitable.

The surface-active agent may be an emulsifying agent or a dispersing agent or a wetting agent; it may be nonionic or ionic. Any of the surface-active agents usually applied in formulaing herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 1–5% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or a surface-active agent, and are diluted in the field with further solid carrier to give a composition usually containing $\frac{1}{2}$–10% by weight of toxicant. Granules are usually prepared to have a size between 10 and 100 BS mesh (1.676–0.152 mm), and may be manufactured by agglomeration or impregnation techniques. Generally granules will contain $\frac{1}{2}$–25% by weight toxicant and 0–10% by weight of additives such as stabilizers, slow release modifiers and binding agents. Emulsifiable concentrates usually contain, in addition to the solvent and, when necessary, co-solvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5–5% w of dispersing agents, 1–5% of surface-active agent, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compounds of this invention comprises applying a compound of formula I, ordinarily in a composition of one of the aforementioned types, to a locus or area to be protected from undesirable plant growth such as the foliage of the plant or the plant growth medium, e.g. soil in which the plant is growing or is to be grown. The active compound of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identities of all compounds, intermediates, and final, were confirmed by elemental analysis, and infrared and nuclear magnetic spectral analyses. The examples are for the purpose of illustration only and should not be regarded as limiting the invention in any way.

EXAMPLE 1

N-((5-chloro-6-(isopropoxy)-3-pyridinyl)-1-methylcyclopropanecarboxamide (a) 2-hydroxy-5-nitropyridine A mixture containing 500 g (3.6 mol) of 2-amino-5-nitropyridine in 2000 ml of 10% sodium hydroxide was refluxed at about 102° C. for 10 hours, cooled and filtered. The filter cake was dissolved in water and neutralized with hydrochloric acid. The product was filtered and dried to give 301.7 g (60%) of product as a white powdery solid, m.p. 188°-190° C.

(b) 3-chloro-2-hydroxy-5-nitropyridine

To a warm (50° C.) mixture of 100.1 g (0.72 mol) of 1a above in 800 ml of concentrated hydrochloric acid was added dropwise with stirring a solution of 70.0 g (0.6 mol) of potassium chlorate in 1300 ml of water causing an exothermic reaction. The rate of addition was adjusted so that the internal temperature was maintained between 48° and 50° C. After the addition was complete, the reaction temperature was maintained at 50° C. for two additional hours. After cooling to about 10° C. and filtering, the filter cake was washed with 500 ml of water and dried to give 92.0 g (59%) of product as a yellow solid; m.p. 195°-197° C.

(c) 3-chloro-2-(isopropoxy)-5-nitropyridine

To a mixture containing 8.73 g (0.05 mol) of 1b above and 12.6 g (0.1 mol) of isopropyl bromide in 50 ml of dimethyl sulfoxide was added portionwise 2.4 g (0.057 mol) of 57% sodium hydride. The reaction mixture was stirred and heated at 40° C. for 13 hours, cooled and poured into water. The acidified mixture was extracted with ether and dried. Silica chromatography afforded 2.5 g (27%) of product as an amber liquid.

(d) N-((5-chloro-6-(isopropoxy)-3-pyridinyl)-1-methylcyclopropanecarboxylate

A solution of 2.0 g (0.009 mol) of 1c above in 75 ml of tetrahydrofuran was hydrogerated over Raney-nickel using a Parr shaker. The mixture was filtered and the filtrate was successively treated with 1.5 g of triethylamine and 1.2 g of 1-methylcyclopropanecarbonyl chloride. After 12 hours at ambient temperature, the reaction mixture was concentrated to dryness, washed with water and extracted into ether. Silica chromatography of the ether extract gave 1.5 g (63%) of product, m.p. 116°-117° C.

EXAMPLE 2

N-((5-chloro-6-(isopropylmethylamino)-3-pyridinyl)-1-methylcyclopropanecarboxamide (a) 2,3-Dichloro-5-nitropyridine A mixture of 140.4 g (0.83 mol) of 1b above and 191.5 g (0.92 mol) of phosphorus pentachloride in 150 ml of phosphorus oxychloride was heated at 140° for 1.5 hours. The cooled reaction mixture was poured into 2000 ml of ice water and filtered. The filter cake was dissolved in ether, dried and concentrated to a volume of about 200 ml. Hexane was added to the solution to cause the product to precipitate as a solid to give 52.9 g (33%); m.p. 52° C.

(b) 3-chloro-2-(isopropylmethylamino)-5-nitropyridine

To a solution containing 19.3 g (0.1 mol) of 2a above in 130 ml of dimethyl sulfoxide was added 14.6 g (0.2 mol) of isopropylmethylamine causing the temperature to rise to 55° C. The reaction mixture was stirred at ambient temperature for 1.5 hours and poured into 1000 ml of ice water. The product was filtered, washed with water and dried to give 18.2 g (75%) of light tan solid, m.p. 56°-57° C.

(c) N-((5-chloro-6-(isopropylmethylamino)-3-pyridinyl)-1-methylcyclopropanecarboxamide.

A solution of 5.75 g (0.025 mol) of 2b above in 75 ml of tetrahydrofuran was reduced over Raney-nickel in a Parr shaker for 2 hours at ambient and 50 pounds of hydrogen pressure. To the filtered solution containing the corresponding aminopyridine was added one molar equivalent of triethylamine and one molar equivalent of 1-methylcyclopropanecarbonyl chloride. The usual work-up of the reaction mixture gave 4.1 g (58%) of product as a white solid; m.p. 86°-87° C.

EXAMPLE 3

N-(5,6-dichloro-3-pyridinyl)-1-methylcyclopropanecarboxamide

A solution containing 4.8 g (0.025 mol) of 2a above in 150 ml of tetrahydrofuran was hydrogenated for 1.5 hours at about 25° C. and 53 pounds hydrogen pressure over Raney-nickel. To the filtered solution containing the corresponding aminopyridine was added 2.5 g of triethylamine and 2.96 g of 1-methylcyclopropanecarbonyl chloride in 20 ml of tetrahydrofuran. The reaction mixture was refluxed for 45 minutes, cooled and concentrated. The residue was diluted with water and extracted with ether. Recrystallization from ether-hexane gave 2.2 g (36%) of product as a white solid; m.p. 115°-117° C.

EXAMPLES 4–14

Using procedures similar to those described in Examples 1–3, additional amides of the invention were prepared as identified in Table I.

TABLE I

N-(3-pyridinyl)cyclopropanecarboxamides

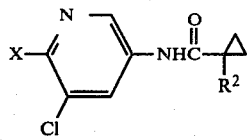

| Example No. | R¹ | X | % yield | m.p., ° C. |
|---|---|---|---|---|
| 4 | H | Cl | 57 | 159–160 |
| 5 | H | (CH$_3$)$_2$N— | 32 | 130–131 |
| 6 | CH$_3$ | (CH$_3$)$_2$N— | 50 | 91–93 |
| 7 | H | (CH$_3$)$_2$CHNH— | 44 | 133–135 |
| 8 | CH$_3$ | (CH$_3$)$_2$CHNH— | 55 | 86–87 |
| 9 | H | (CH$_3$)$_3$CNH— | 72 | 129–130 |
| 10 | CH$_3$ | (CH$_3$)$_3$CNH— | 38 | 110–112 |
| 11 | H | ![cyclopropyl-CH3-NH—] | 61 | 158–160 |
| 12 | CH$_3$ | ![cyclopropyl-CH3-NH—] | 57 | 100–102 |
| 13 | H | (CH$_3$)$_2$CHN(CH$_3$)— | 55 | 147–148 |
| 14 | CH$_3$ | (CH$_3$)$_2$CHS— | 21 | 113–115 |

EXAMPLE 15

N-(5-chloro-6-(1-methylcyclopropylamino)-3-pyridinyl)-N'-methyl-N'-methoxyurea 5.0 g of N-(3-chloro-5-nitro-pyridin-2-yl)-N-(1-methylcyclopropyl)amine was reduced in a Parr bomb in tetrahydrofuran solvent with Raney-nickel as catalyst. When the reduction was complete, the reaction mixture was dried with MgSO$_4$ and then filtered to remove catalyst and MgSO$_4$. The filtrate was put in a 1 liter flask to which was added 2.5g of triethylamine and 2.7g of methoxymethylcarbamoyl chloride. The flask fitted with a drying tube was left to stand at ambient temperature.

The next day reaction mixture was stripped to dryness. Water was added to the resulting residue. Then the residue was extracted with ether and the extract was dried over MgSO$_4$. Hexane was added to the dried extract. The volume of the resulting solution was reduced on a steam bath. The resulting precipitate was filtered and dried in vacuo to yield 3.1g (49%) of product; m.p. 76°–78° C.

EXAMPLES 16–20

Using procedures similar to that described in Example 15, additional ureas of the invention were prepared as identified in Table II.

TABLE II 3-pyridinylureas

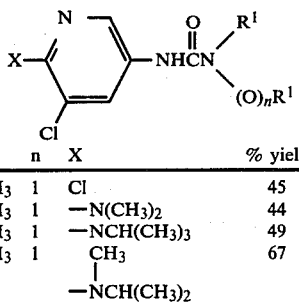

| Example | R¹ | n | X | % yield | m.p., ° C. |
|---|---|---|---|---|---|
| 6 | CH$_3$ | 1 | Cl | 45 | ca 50° |
| 7 | CH$_3$ | 1 | —N(CH$_3$)$_2$ | 44 | 92–94 |
| 8 | CH$_3$ | 1 | —NCH(CH$_3$)$_3$ | 49 | 105–106 |
| 19 | CH$_3$ | 1 | CH$_3$<br>|<br>—NCH(CH$_3$)$_2$ | 67 | 98–99 |

TABLE II-continued 3-pyridinylureas

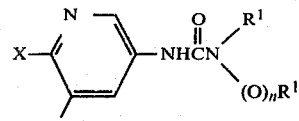

| Example | R¹ | n | X | % yield | m.p., ° C. |
|---|---|---|---|---|---|
| 20 | CH$_3$ | 1 | —NHCH(CH$_3$)$_2$ | 45 | 69–71 |

EXAMPLE 21

N-(5-chloro-6-(dimethylamino)-3-pyridinyl)-N',N'-dimethylurea (a) 3-chloro-2-(dimethylamino)-5-nitropyridine 9.0 g (0.2 mol) of dimethylamine was introduced into a solution containing 19.3 g (0.1 mol) of 2a above in 200 ml of tetrahydrofuran. This addition was exothermic to 45° C. After 1.5 hours, the reaction mixture was concentrated under reduced pressure. The residue was diluted with 300 ml of water and extracted with ether. Concentration of the ether extract and addition of hexane gave 17.8 g (88% yield) of product; m.p. 111°–113° C.

(b)
N-(5-chloro-6-(dimethylamino)-3-pyridinyl)-N',N'-dimethylurea

A solution of 6.1 g (0.03 mol) of 21a above in 75 ml of tetrahydrofuran was hydrogenated over Raney-nickel in a Parr shaker. The reaction mixture was filtered and the filtrate was concentrated to dryness. The residue was dissolved in 40 ml of pyridine and treated with 6.5 g (0.06 mol) of dimethylcarbamoyl chloride on a steam bath for 15 minutes. The cooled reaction mixture was poured into 750 ml water, extracted with ether, dried and concentrated to dryness. The residual red oil crystallized from ether-hexane to give 4.1 g (56% yield) of product as a white solid; m.p. 139°–141° C.

Example of Herbicidal Activity

The pre-emergence herbicidal activity of the compounds of the invention was evaluated by planting seeds of watergrass, garden cress, downey brome, velvet leaf, yellow foxtail and sicklepod in test tubes, nominally measuring 25×200 millimeters, containing soil treated with the test compound at the rates of 0.1 and 1 mg per tube designated in Table III at Rates I and II respectively. The planted soil was held under controlled conditions of temperature, moisture, and light for 11 to 12 days. The amount of germination and growth in each tube were evaluated on a 0 to 9 scale, 0 rating indicating no effect, 9 death of the seedlings or no germination.

The post-emergence activity of the compounds of this invention was evaluated by spraying 7-day old crabgrass plants, 10-day old pigweed plants, 6-day old downey brome plants, 8-day old velvet leaf, 7-day old sicklepod plants, and 10-day old yellow foxtail plants to runoff with a liquid formulation of the test compound at the rates of 0.8 milliliter of an 0.025 solution designated as Rate I in Table III and 0.8 milliliter of an 0.25% solution designated as Rate II in Table III. The sprayed plants were held under controlled conditions for 10 to 11 days and the effect of the test compound was then evaluated visually, the results being rated on the 0 to 9 scale described above.

The results of the pre- and post-emergence tests are summarized in Table III.

TABLE III

HERBICIDE RESULTS

| | Pre-emergence (soil) | | | | | | Post-emergence (Foliar) | | | | | |
|---|---|---|---|---|---|---|---|---|---|---|---|---|
| Ex. | Watergrass I / II | Garden Cress I / II | Downey Brome I / II | Velvet Leaf I / II | Yellow Foxtail I / II | Sicklepod I / II | Crabgrass I / II | Pigweed I / II | Downey Brome I / II | Velvet Leaf I / II | Yellow Foxtail I / II | Sicklepod I / II |
| 3 | 4 / 8 | 9 / 9 | 7 / 8 | 7 / 9 | 0 / 8 | 7 / 9 | 4 / 9 | 3 / 9 | 2 / 8 | 3 / 9 | 8 / 9 | 4 / 9 |
| 4 | 4 / 6 | 9 / 9 | 7 / 7 | 9 / 9 | 0 / 9 | 7 / 9 | 2 / 6 | 2 / 9 | 3 / 3 | 0 / 9 | 6 / 9 | 4 / 9 |
| 13 | 3 / 5 | 9 / 9 | 8 / 8 | 9 / 9 | 4 / 4 | 7 / 7 | 2 / 4 | 2 / 9 | 0 / 3 | 2 / 8 | 7 / 9 | 5 / 9 |
| 2 | 3 / 6 | 9 / 9 | 7 / 8 | 8 / 9 | 0 / 8 | 7 / 8 | 2 / 6 | 2 / 9 | 2 / 9 | 2 / 8 | 8 / 9 | 5 / 8 |
| 14 | 2 / 2 | 7 / 8 | 0 / 0 | 0 / 0 | 0 / 0 | 0 / 0 | 6 / 9 | 8 / 9 | 6 / 7 | 7 / 9 | 7 / 9 | 4 / 6 |
| 6 | 0 / 7 | 7 / 8 | 0 / 4 | 0 / 8 | 0 / 9 | 5 / 8 | 2 / 8 | 3 / 9 | 4 / 7 | 5 / 9 | 6 / 9 | 6 / 8 |
| 12 | 3 / 6 | 7 / 8 | 6 / 6 | 5 / 9 | 4 / 7 | 4 / 8 | 2 / 5 | 0 / 9 | 0 / 3 | 3 / 8 | 3 / 8 | 4 / 8 |
| 8 | 6 / 7 | 8 / 9 | 6 / 8 | 9 / 9 | 5 / 8 | 6 / 8 | 2 / 3 | 2 / 4 | 0 / 3 | 2 / 6 | 5 / 8 | 5 / 8 |
| 10 | 3 / 4 | 8 / 9 | 3 / 7 | 6 / 7 | 3 / 4 | 0 / 3 | 3 / 8 | 2 / 6 | 2 / 6 | 5 / 7 | 7 / 8 | 3 / 7 |
| 1 | 6 / 7 | 7 / 8 | 8 / 9 | 8 / 8 | 0 / 7 | 4 / 7 | 8 / 9 | 7 / 9 | 8 / 9 | 9 / 9 | 9 / 9 | 9 |
| 7 | 5 / 7 | 8 / 9 | 8 / 8 | 9 / 9 | 5 / 8 | 6 / 6 | 4 / 5 | 5 / 9 | 0 / 8 | 3 / 9 | 5 / 9 | 5 / 8 |
| 9 | 0 / 5 | 7 / 9 | 0 / 4 | 0 / 5 | 0 / 5 | 0 / 3 | 4 / 8 | 2 / 9 | 3 / 6 | 5 / 7 | 4 / 8 | 4 / 8 |
| 11 | 0 / 4 | 0 / 8 | 3 / 7 | 4 / 9 | 0 / 7 | 0 / 6 | 5 / 5 | 3 / 7 | 2 / 4 | 4 / 8 | 5 / 9 | 6 / 8 |
| 17 | 6 / 8 | 8 / 9 | 7 / 9 | 8 / 9 | 7 / 9 | 8 / 9 | 2 / 5 | 2 / 6 | 0 / 5 | 2 / 6 | 3 / 8 | 4 / 8 |
| 20 | 6 / 7 | 8 / 9 | 7 / 8 | 9 / 9 | 5 / 8 | 4 / 8 | 6 / 6 | 4 / 8 | 0 / 4 | 2 / 7 | 3 / 7 | 4 / 8 |
| 15 | 0 / 4 | 6 / 7 | 2 / 8 | 4 / 9 | 0 / 6 | 3 / 8 | 0 / 4 | 4 / 3 | 0 / 7 | 4 / 4 | 4 / 9 | 5 / 8 |
| 19 | 4 / 6 | 8 / 9 | 5 / 7 | 8 / 9 | 4 / 7 | 7 / 9 | 4 / 9 | 2 / 9 | 6 / 7 | 3 / 9 | 4 / 9 | 4 / 9 |
| 18 | 4 / 5 | 6 / 7 | 6 / 7 | 9 / 9 | 3 / 7 | 4 / 7 | 3 / 8 | 2 / 9 | 4 / 9 | 6 / 9 | 6 / 9 | 7 / 8 |
| 16 | 3 / 6 | 6 / 9 | 7 / 9 | 8 / 8 | 6 / 8 | 4 / 8 | 2 / 9 | 5 / 9 | 2 / 8 | 7 / 9 | 8 / 9 | 7 / 9 |

I claim:

1. A compound of the formula

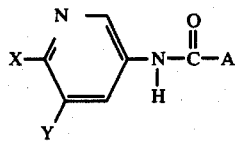

wherein
A is

in which $R^2$ is a hydrogen atom or a methyl group;
Y is a halogen atom having an atomic number of from 9 to 35, inclusive; and
X is a halogen atom having an atomic number of from 9 to 35, inclusive; $-NR^3R^4$ in which $R^3$ and $R^4$ each independently is a hydrogen atom or an alkyl group containing from 1 to 6 carbon atoms or $R^4$ is additionally a cycloalkyl group containing from 3 to 7 ring carbon atoms and 3 to 11 carbon atoms; or $OR^5$ in which $R^5$ is an alkyl group containing from 1 to 6 carbon atoms.

2. A compound of the formula

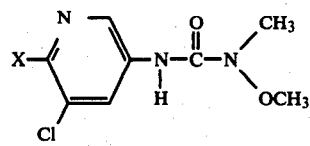

wherein X is chlorine or $-NR^3R^4$ in which $R^3$ and $R^4$ each independently is a hydrogen atom or an alkyl group containing from 1 to 6 carbon atoms or $R^4$ is additionally a cycloalkyl group containing from 3 to 7 ring carbon atoms and 3 to 11 total carbon atoms.

3. A compound according to claim 1 wherein Y is chlorine.

4. A compound according to claim 3 wherein X is a halogen atom having an atomic number of from 9 to 35, inclusive; $-NR^3R^4$ in which $R^3$ and $R^4$ each independently is a hydrogen atom or an alkyl group containing from 1 to 4 carbon atoms or is methylcyclopropyl, or X is $OR^5$ in which $R^5$ is an alkyl group containing from 2 to 3 carbon atoms.

5. A compound according to claim 4 wherein $R^2$ is methyl and X is chlorine.

6. A compound according to claim 4 wherein $R^2$ is a hydrogen atom and X is chlorine.

7. A compound according to claim 4 wherein $R^2$ is methyl and X is isopropylmethylamino.

8. A compound according to claim 2 wherein X is chlorine.

9. A compound according to claim 2 wherein X is dimethylamino.

10. A compound according to claim 2 wherein X is tertiarybutylamino.

11. A compound wherein X is isopropylmethylamino.

12. An herbicidal composition comprising a herbicidally effective amount of a compound according to claim 1 and at least one surface-active agent or carrier therefore.

13. A method for controlling undesirable plant growth at a locus to be protected which comprises applying to the locus to be protected a plant growth controlling amount of a compound according to claim 1 or a composition thereof.

* * * * *